(12) United States Patent
Seljelid (10) Patent No.: US 8,946,193 B2
(45) Date of Patent: Feb. 3, 2015

(54) MEDICAL USES OF GLUCANS

(75) Inventor: Rolf Seljelid, Tromsø (NO)

(73) Assignee: Biotec Pharmacon ASA, Tromsø (NO)

( * ) Notice: Subject to any disclaimer, the term of this patent is extended or adjusted under 35 U.S.C. 154(b) by 155 days.

(21) Appl. No.: 13/561,353

(22) Filed: Jul. 30, 2012

(65) Prior Publication Data
US 2012/0295868 A1 Nov. 22, 2012

Related U.S. Application Data

(63) Continuation of application No. 12/528,215, filed as application No. PCT/GB2008/000609 on Feb. 21, 2008, now abandoned.

(30) Foreign Application Priority Data

Feb. 21, 2007 (EP) .................. 0703356
Feb. 22, 2007 (EP) .................. 0703474

(51) Int. Cl.
| A01N 43/04 | (2006.01) |
| A61K 31/715 | (2006.01) |
| A61K 31/716 | (2006.01) |

(52) U.S. Cl.
CPC ............................. *A61K 31/716* (2013.01)
USPC ........................................................ 514/54

(58) Field of Classification Search
CPC .................................................. A61K 31/716
USPC ........................................................ 514/54
See application file for complete search history.

(56) References Cited

U.S. PATENT DOCUMENTS

| 5,401,727 | A * | 3/1995 | Rorstad et al. ............. 514/54 |
| 6,242,594 | B1 * | 6/2001 | Kelly ................... 536/123.12 |
| 2002/0009463 | A1 * | 1/2002 | Raa et al. ................ 424/204.1 |
| 2004/0248772 | A1 | 12/2004 | Yagita |
| 2006/0205679 | A1 | 9/2006 | Streeper |
| 2009/0246287 | A1 * | 10/2009 | Shoseyov .................... 424/499 |

FOREIGN PATENT DOCUMENTS

| WO | 9530022 A1 | 11/1995 |
| WO | 0162283 A2 | 8/2001 |
| WO | 0212348 A2 | 2/2002 |
| WO | WO 2004/037232 A1 * | 5/2004 | .............. A61K 9/50 |

OTHER PUBLICATIONS

Definition of "prevention" from the Institute for International Medical Education [online], [Retrieved on Mar. 24, 2011]. Retrieved from the internet <http://www.iime.org/glossary.htm>. Published Feb. 2002, p. 1, 2, 26, 27 and 39.*
"Fact Sheet: Allergic Rhinitis (Hay Fever)" from American Academy of Otolaryngology—Head and Neck Surgery [online]. Retrieved on Mar. 11, 2013. Retrieved from the internet <http://www.entnet.org/HealthInformation/allergicRhinitis.cfm>.*
"Hay Fever (Rhinitis)" from the Virtual Pediatric Hospital [online]. Retrieved on Mar. 11, 2013. Retrieved from the internet <http://www.virtualpediatrichospital.org/patients/cqqa/hayfever.shtml>.*
Kirmaz, C., Bayrak, P., Yilmz, O., Yuksel, H. (2005) Effects of glucan treatment on the Th1/Th2 balance in patients with allergic rhinitis: a double-blind placebo-controlled study. European Cytokine Network, vol. 16, No. 2, p. 128-134.*
Product Information Sheet on "Imuneks" by MN Pharmaceuticals [online]. Retrieved on Mar. 11, 2013. Retrieved from the Internet <http://www.mn.com.tr/products/pdf/Imuneks_50mg.pdf>.*
Ansel, H.C., Allen, Jr., L.V., Popovich, N.G. (1999) Pharmaceutical Dosage Forms and Drug Delivery Systems. Published by Lippincott Williams & Wilkins, p. 23-59.*
Benson, M, Strannegård, I.-L., Wennegren, G., Strannegård, Ö. (2000) Low levels of interferon-γ in nasal fluid accompany raised levels ot T-helper 2 cytokines in children with ongoing allergic rhinitis. Pediatric Allergy and Immunology, vol. 11, p. 20-28.*
Ciprandi, G., Cirillo, I., Klersy, C., Marseglia, G.L., Caimmi, D., Vizzaccaro, A. (2005) Nasal Obstruction is the Key Symptom in Hay Fever Patients. Otolaryngology—Head and Neck Surgery, vol. 133, p. 429-435.*
Oh, et al., "*Streptomyces cerevisiae* 1,3/1,6 beta-gucan prevents airway hyperreactivity and pulmonary inflammation in a murine asthma model," Journal of Allergy and Clinical Immunology, 119(1, Supp 1): S6, Jan. 2007.
Biotec Phrmacon Offering Circular [online], pp. 1-75 (Oct. 6, 2005), retrieved from the internet: http://www.biotec.n/files/Biotec_Phar.
"Modulation of immune reactions by beta-1,3/1,6-glucan" Mongraph, [online] pp. 1-17, Jan. 1, 2004. Retrieved from the internet: http://ww.nbg247.no/getfile.php/files/HUMAN_Monograph_January_2004.pdf.
Ziatkovic, D., et al., "A glucan from active dry baker's yeast (*Saccharomyces cerevisiase*): A chemical and enzymatic investigation of the structure," Journal of Serbian Chemical Society, vol. 68, No. 11, pp. 805-809 (2003).
Tsukada, C., et al., "Immunopotentiation of intraepithelial lymphocytes in the intestine by oral adminsatraion of β-glucan," Cellular Immunology, vol. 221, pp. 1-5 (2003).

* cited by examiner

*Primary Examiner* — Scarlett Goon
(74) *Attorney, Agent, or Firm* — Rothwell, Figg, Ernst & Manbeck (57) ABSTRACT

The invention relates to a glucan having a beta-(1,3)-backbone with one or more beta-(1,3)-side chains linked thereto for use in the treatment of asthma and related diseases of abnormal pulmonary function in an animal. Also described is a method of treating asthma and related diseases of abnormal pulmonary function in an animal comprising administering to said animal an effective amount of a glucan having a beta-(1, 3)-backbone with one or more beta-(1,3)-side chains linked thereto.

9 Claims, 8 Drawing Sheets

MEDICAL USES OF GLUCANS

This application is a continuation of U.S. Ser. No. 12/528,215, filed 29 Jul. 2010 which is a filing under 35 USC 371 of PCT/GB2008/000609, filed 21 Feb. 2008, which claims priority from GB 0703356.6, filed 21 Feb. 2007 and GB 0703474.7, filed 22 Feb. 2007. All of these prior applications are incorporated herein by reference.

The present invention relates to the use of glucans for treating asthma and related diseases of abnormal pulmonary function.

Glucans are a heterogeneous group of glucose polymers found in the cell walls of plants, bacteria and fungi. The basic structural unit in beta-glucans is a backbone chain comprising or consisting of β(1→3)-linked glucosyl units. Depending upon the source and method of isolation, beta-glucans have various degrees of branching and of linkages in the side chains. The frequency and type of linkage in the side chains determine the molecule's biological activity. Beta-glucans of fungal and yeast origin are normally insoluble in water, but can be made soluble either by acid hydrolysis or by derivatization introducing foreign groups like -phosphate, -sulphate, -amine, -carboxymethyl and so forth to the molecule.

In Europe, Asia and USA, beta-glucans especially from Bakers' yeast have long been employed as feed additives for animals, as dietary supplement for humans, in treatment of wounds, and as an active ingredient in skin cream formulations. Further, glucans have been employed as functional pharmaceutical agents exemplified by their application for treatment of cancer as shown in WO02058711. Different glucans have very different activities in vivo and it is usually hard to predict which glucan would be most effective for a given therapy and not possible to assume that a particular glucan will be active just because a glucan with a different structure has been shown to have that activity.

Asthma is a chronic inflammatory lung disease characterized by dyspnoea, superimposed infections, mild to grave impairment of general health, in some cases leading to a painful death. The prevalence of the disease has increased markedly over the last few decades such that about one in ten persons in industrialized countries carry the diagnosis. The efficacy of available therapy is modest and there is no known effective prophylaxis. The impact of the disease on public health is therefore serious, related health care expenditures enormous and increasing.

The observation that the prevalence of asthma has increased dramatically over the past two decades while certain environmental exposures (e.g. exposure to infectious diseases) have decreased, suggests that certain infections may reduce the risk of developing asthma, presumably by enhancing the development of protective immunity. These observations are the basis for the 'hygiene hypothesis', which suggests that improved hygiene in industrialized societies, which improved public health measures and the use of vaccines and antibiotics, has reduced the incidence of infections and the exposure to environmental factors that would normally stimulate the immune system in a way that mitigates against asthma.

At present asthma is not cured, it is managed, through careful control of the patient's environment, measurements of lung function to anticipate an attack and through medication. Medication includes anti-inflammatory drugs which reduce the spontaneous spasm of the muscles of the airways and bronchodilators which increase the diameter of the air passages and thereby the flow of gases to and from the lungs.

Asthma is caused by dysregulated immune responses in the respiratory mucosa. It is believed that Th2(T helper 2)-driven responses play a crucial role in the pathogenesis, particularly because typical Th2 cytokines are involved: interleukin 4 (IL4) and IL-13 enhance IgE production, IL-4, IL-9 and IL-10 enhance mast cell activity, IL-5 enhance eosinophil accumulation and IL-9 and IL-13 directly enhance mucus secretion and airway hyperactivity—all of these phenomena typical of asthma.

Although it is generally accepted that Th2-driven immune reactions are involved in the development of asthma and related diseases of abnormal pulmonary function, the exact pathogenesis is not understood, nor are the protective mechanisms in non-asthmatic individuals. Although all individuals are exposed to allergens and other sensitizing agents in the environment, asthma develops only in some of the exposed, suggesting that both environmental and genetic factors play important roles in determining the development of pathogenic Th2 responses.

JP 2002335926 suggests the use of a glucan containing formulation for treating a wide variety of different conditions including HIV, diabetes and asthma. The glucans here are unbranched or have 1,6-linked single or multiple glucopyranose units and do not have 1,3-linked side chains.

Surprisingly, the inventors of the present invention found that asthma and related diseases of abnormal pulmonary function might be treated by using a certain class of glucan.

Even though extensive studies have been performed on asthma and related diseases and conditions, no single effective and patient-compliant method and substance has been found for the treatment and/or prevention of these illnesses. The present invention addresses this problem, proposing the use of certain glucans for preventing and/or treating asthma and related pulmonary diseases.

Thus, in one aspect, the invention provides the use of a glucan having a beta-1,3 backbone with one or more beta-1,3 side chains linked thereto, in the manufacture of a medicament for the treatment of asthma or related diseases of abnormal pulmonary function.

Alternatively viewed, the invention provides a glucan having a beta-1,3 backbone with one or more beta-1,3 side chains linked thereto for use in the treatment of asthma or related diseases of abnormal pulmonary function.

The glucan has a beta-1,3 backbone, i.e. the backbone is made up of beta-1,3 linked glucopyranose units. The glucan has beta-1,3 side chains, i.e. attached to the backbone via a beta-1,6 linkage are one or more side chains made up of beta-1,3 linked glucopyranose units. Thus the side chain comprises 2 or more, typically 3, 4, 5, 10 or more beta-1,3 linked glucopyranose units.

Thus, preferably less than 10%, more preferably less than 5%, most preferably less than 3% or 2% of the glycosidic bonds in the glucan molecule will be beta-(1,6)-linkages.

Preferably the glucan moiety is underivatised by chemical groups, at least, it preferably does not contain the following groups: sulfate, acetate, phosphate or phosphonate.

In the present invention the glucan is administered to a subject by any possible mode of administration, but preferably orally.

The medicament may be administered as part of a dietary regimen. The medicament may be formulated as a nutraceutical, animal feed, food, part of a nutraceutical, animal feed or food and/or adjuvant. The glucan containing medicaments may be administered to any animal, including humans, non-human primates and other mammals, domestic and livestock animals, birds, and fish, including farmed birds and companion birds like parrots, and farmed fish and pet fish. Specific examples include dog, cat, horse, cow, pig, goat, rat, mouse and sheep. Humans are preferred recipients.

The glucan of use according to the invention is not part of a natural whole product, e.g. a plant which may have within it protein and glucan. Thus the glucan can be considered a processed product. It may be considered isolated in the sense that it is no longer part of the whole cell or organism from which it originates, preferably it is no longer in admixture with all the other cell wall components which it is found with in nature. Preferably the glucan is also processed in the sense that the chemical structure is altered as compared to the naturally occurring structure as well as being isolated (at least partially) from other naturally occurring cell-wall components. The alterations will typically comprise reductions in length of the backbone and/or in length or complexity of branches.

The glucan can be from a variety of different sources. Important and preferred sources are yeasts as exemplified by *Saccharomyces cerevisiae*. The yeast cell wall consists mainly of polysaccharides made up of three sugars, glucose, mannose, and N-acetylglucosamine. The mannose polysaccharides are linked to proteins to form a mannoprotein layer mainly localized at the external surface.

Glucans from yeast consist essentially of a beta-1,3 backbone and side chains which are generally linked via a beta-1,6-linkage to the backbone structure. Therefore beta-glucans from yeast and other organisms producing glucans with a similar structure are often described as beta-1,3/1,6; beta-1,3 or simply beta-glucans.

Preferred beta-glucan containing products for use according to the invention contain at least 75%, preferably at least 80%, carbohydrate as a percentage of total cell components. Of this carbohydrate, the majority is glucan.

Examples of useful beta-glucan products for the present invention include, but are not limited to, the glucan products Imucell as manufactured by Biothera and Immiflex (formerly Fluflex) as distributed by CarePharma Co, Ltd.

Particularly preferred beta-glucans include, but are not limited to, particulate and soluble yeast cell wall glucans as described in PCT/IB95/00265 and EP 0759089. Depending upon yeast strain and type, glucan constitutes up to 25% of the yeast cell wall dry weight. During the process of isolating beta-glucan from yeast the outer layer of mannoprotein is removed as well as most of the inner content of the cell, leaving a "ghost" particle, or whole glucan particle, constituting the beta-glucan layer. If the beta-glucan is isolated from autolysed yeast, the cell wall is more collapsed giving a crumpled ghost particle.

Brewers yeast differs in composition from bakers yeast because it is grown under anoxic conditions, resulting in a lower level of beta-glucan in the cell walls. Other yeasts which provide a source for the glucan include *Candida* sp., *Hansenula* sp., *Histoplasma* sp., *Kloeckera* sp., *Kluyveromyces* sp., *Pichia* sp., *Rhodotorula* sp., *Saccharomyces* sp., *Schizophyllum* sp., *Schizosaccharomyces* sp., *Torula* sp. and *Torulopsis* sp.

As discussed above, surprising efficacy has been shown for a glucan having a beta-1,3 backbone with one or more beta-1,3 side chains linked thereto. Such glucans may also be sourced from some of the following known glucan sources.

Other sources of glucan are mushrooms or other fungi exemplified by those belonging to the classes Mastigomycotina, Ascomycotina, Basidiomycotina, and Deuteromycotina (imperfect fungi). Other suitable fungi include *Aspergillus* sp., *Penicillium* sp., *Sclerotinia* sp., and *Sclerotum* sp.

A third source of glucan are the members of the Gramineae (grasses), amongst the Angiosperms, where they are major components of endosperm walls of commercially important cereals such as oat, barley, rye, sorghum, rice and wheat. Apart from these, plants are not preferred sources.

A fourth source of glucan are algae, exemplified by the classes Chlorophyceae, Charophyceae Euglenophyceae, Phaeophyceae, Bacillariophyceae, Chrysophyceae, Xanthophyceae, Pyrrophyceae and Rhodophyceae. Laminarin is an example for a glucan product from sea-weed.

It is also possible to derive said glucan from the cell walls of Bacteria like Alcaligenes (Achromobacteriaceae), *Agrobacterium* and *Rhizobium* (Rhizobacteriaceae). Examples are *Alcaligenes faecalis, Agrobacterium radiobacter* and *A. rhizogenes, Rhizobium japonicum og R. trifolii, Streptococcus pneumoniae* as well as the Cyanobacteriaceae *Anabaena cylindrica*. Finally, also the glucan from *Streptococcus feacalis* which is the origin for the glucan Curdlan may be used in connection with the present invention.

In the animal feed and farming industry the cells of organisms, most often yeast cells, are used, and fed directly to the animals. These products come in different forms and shapes, like compressed, liquid, crumbled, dry, active, in-active cells, and combinations like active dry, instant active dry and inactive dry. These products are most often the remnants of the cells used for other production processes like brewing or baking.

Likewise, beta-glucan formulations solublized by derivatization, e.g., glucan amines or carboxymethyl-glucans are possible active products.

It is convenient to use processed products or cell extracts to achieve the effect of the present invention. These products may be hydrolysed or autolysed cells, partially or completely purified cell walls. All these products are available in various forms suited to different types of use: liquid, semi-paste, paste, fine powder, oil-coated powder, micro-granulated powder, to mention only some.

Products containing isolated carbohydrate components may be combination products of two or more components (e.g. from the yeast cell wall), for example a combination of glucans and mannans.

The glucan may be mixed with other components e.g. other parts of the cell wall such as mannans or components not being part of the cell walls, like vitamins or minerals and other agents frequently used in the pharmaceutical, nutraceutical, food, animal feed and veterinary industry. Examples of this group of products are ready to use glucan-products combined with minerals and vitamins as well as nutraceuticals combining glucans and other anti-asthmatic agents.

In addition to the 1,3 linked side chains, the glucan may also have one or more 1,6 linked side chains. However, preferred glucans are those which have been treated by acid or enzyme or any other suitable method to significantly reduce or eliminate the number of repetitive (1,6)-linked glucose molecules within the glucan, or occur naturally with low levels of 1,6 linkages. These (1,6)-linked glucose moieties are mainly in a beta-conformation, and would normally be found in the side chains of the beta-glucan molecule. The number of beta-1,6-linked glucose moieties can vary from one to a significant proportion of the glucose moieties depending on the source of glucan. The resulting preferred glucans have beta-1,3-main chains and beta-1,3 side chains which are linked together by a single beta-1,6-linkage which is not cleaved off by the elimination treatment. These modified glucan molecules are preferably derived from *S. cerevisiae*.

Figure 1:
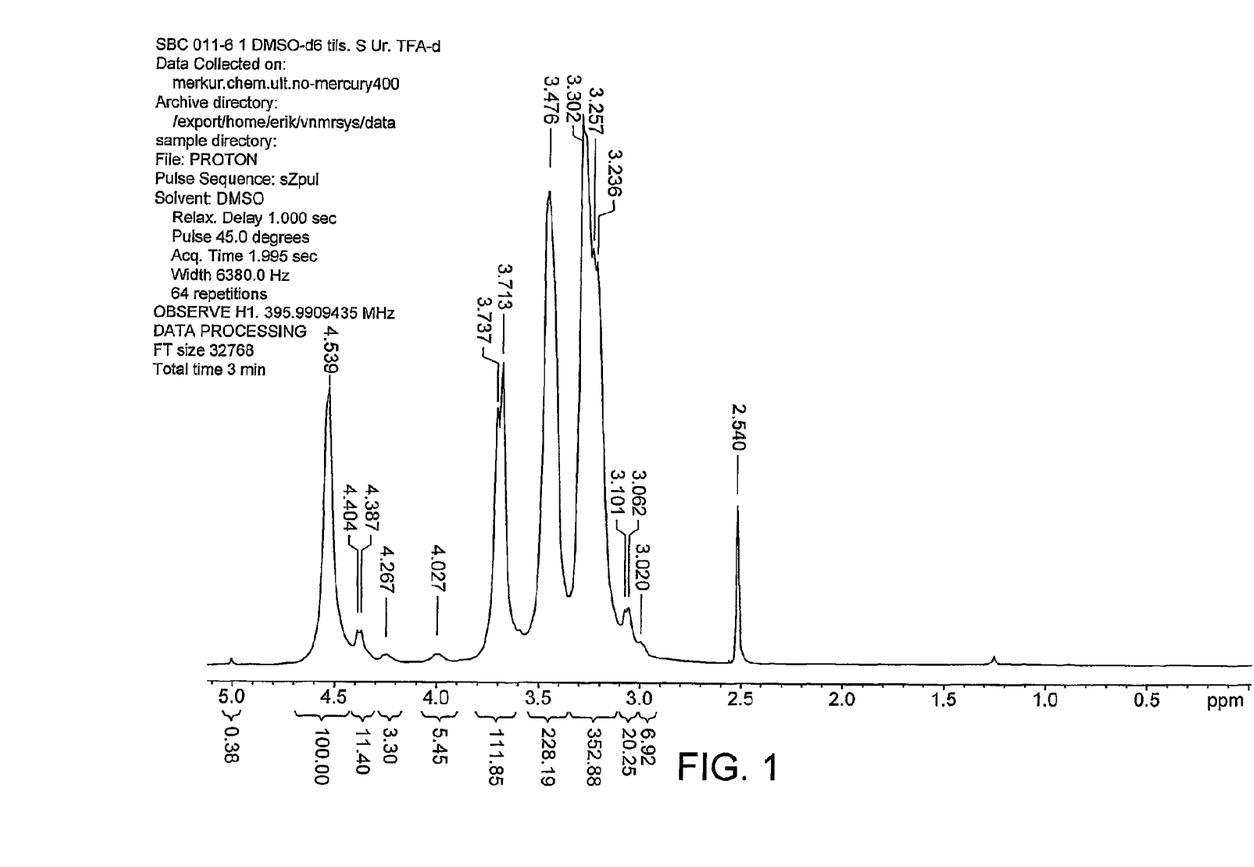
FIG. 1 is an $^1$H-NMR-spectrum of a branched beta-1,3-glucan with <1% repetitive beta-1,6-linked glucosyl units. The different observed chemical shifts are represented in Table 1 below.

The preferred glucans are essentially free of repetitive beta 1,6-linked glucosyl units. Thus, the 1,6-linkages at the branch points do not provide 'repetitive' beta 1,6-linked glucosyl units. By 'essentially free' is meant less than 2%, preferably less than 1% of the total glucosyl units. An example of such a product is seen in FIG. 1 being a ¹H-NMR-spectrum of a branched beta-1,3-glucan with <1% repetitive beta-1,6-linked glucosyl units.

Some treatments, such as enzyme treatments, may leave up to 4 beta-1,6-linked glucosyl units uncleaved in the side chains. Such molecules are also 'essentially free' of repetitive beta 1,6-linked glucosyl units.

The glucan which can be used in relation to the present invention could be in the form of a single, extracted fraction or two or more different fractions with different molecular weights.

The most preferred source for the glucan for the present application are cell walls from *Saccharomyces cerevisiae*. Of these, a preferred source for use in the present invention is the soluble yeast product SBG (Soluble Beta Glucan) as produced by Biotec Pharmacon ASA, a Norwegian based company.

The product is an underivatized (in terms of chemical modifying groups) aqueous soluble beta-1,3/1,6-glucan, characterised by NMR and chemical analysis to consist of polymers of beta-1,3-linked D-glucose containing side-chains of beta-1,3 and beta-1,6-linked D-glucose, wherein the number of beta-1,6 moieties in the side chains (not including at the backbone/side chain branch point) is considerably reduced as compared to the structure of said glucan in the yeast cell wall. An example of such a composition is as follows:

| COMPOSITION | Value/range | typical value |
| --- | --- | --- |
| WATER | 977-983 gram/kg | 980 |
| CARBOHYDRATES | 18-22 gram/kg | 20 |
| PROTEINS | max 1 gram/kg | <1 |
| ASH | max 1 gram/kg | <1 |
| LIPID | Max 1 gram/kg | <1 |

The molecular structure of SBG is as follows:

$n \geq 0$; R=H or $(C_6H_{8-10}O_5)_m$; m (R1+R2)=35 to 2000 glucosyl units.

The reduction of the beta-(1,6)-linked glucosyl residues to produce the above preferred glucan of the present invention may be achieved in one of the following ways:

i) Enzymatic treatment, for example as described in Norwegian Patent No. 300692:
The side chains of beta-1,6-linked glucose in the micro-particulate product prepared as in U.S. Pat. No. 5,401,727 are selectively removed by enzyme treatment with an enzyme which specifically acts on beta-1,6-linkages in a poly-glucose chain. The micro-particulate product (0.2 grams) is suspended in 40 ml 50 mM ammonium acetate buffer at pH 5.0 and mixed with 20 units of the beta-1,6-glucanase enzyme. The mixture is continuously stirred for 6 hours at 37 degrees Celsius and the action of the enzyme stopped by boiling for 5 minutes. The residual enzyme treated particles are washed repeatedly in sterile distilled water by centrifugation and re-suspension. The resulting product is a branched beta-1,3-glucan with beta-1,3-glucan side chains connected by beta-1,6-linked at the branching points, and being essentially free of beta-1,6-linked glucose in the side chains which extend from the branching points. The key step being incubation of a particulate glucan with a beta-1,6-glucanase enzyme at 32 to 40° C. for 3 to 9 hours.

ii) Formic Acid treatment: For example, a micro-particulate product prepared as in U.S. Pat. No. 5,401,727 may be suspended in formic acid and heated. The suspension is cooled and free formic acid removed.

The soluble glucans of the present invention have a molecular weight of greater than 6000 Da, preferably in the range of about 6 kDa to 30 kDA, more preferably in the range from about 10 kDa to 25 kDa, most preferably in the range of about 15 kDa to 20 kDa. When in aqueous solution the molecules may take part in interchain interactions giving a high molecular weight appearance of up to 5000 kDa when analysed by gel performance chromatography.

A preferred glucan containing formulation for use in the invention is a mixture of soluble beta-glucan molecules with molecular weights (MW)>6000 daltons that interact to give a higher order conformation. For example, a mixture of linear beta-1,3-glucan chains with a numerical MW>6 kDa, preferably with a MW ranging from 6-30 kDa, together with branched high molecular weight beta-1,3-glucans (e.g. MW>15 kDa) with beta-1,3 linked side chain(s) extending from within the main chain as shown above.

Preferably, the glucans have an average molecular weight of about 15-20 kDa, with a range from about 6 to about 30 kDa, preferably from about 10 to about 25 kDa. When in aqueous solution the molecules may take part in interchain interactions giving a high molecular weight appearance of up to 5000 kDa when analysed by gel performance chromatography. Preferred compositions are those that form a gel like appearance in aqueous solution, demonstrating complex intermolecular interactions.

Yet another preferred product for use in connection with the present invention is NBG (Norwegian Beta Glucan), a particulate yeast product as produced by Biotec Pharmacon ASA. NBG is a product derived from Bakers Yeast (*Saccharomyces cerevisiae*). The product is a natural underivatized (in terms of chemical modifying groups) particulate beta-1,3/1,6-glucan, characterised by NMR and chemical analysis to consist of polymers of beta-1,3-linked D-glucose containing side-chains of beta-1,3 and beta-1,6-linked D-glucose.

Typical values for the chemical composition of NBG are as follows:

| COMPOSITION | % by weight | Typical range |
|---|---|---|
| CARBOHYDRATES | Min 75 | 75-80 |
| LIPIDS | Max 5 | 3-5 |
| NITROGEN | Max 1.4 | 0.8-1.2 |
| ASH | Max 12 | 8-10 |
| TOTAL SOLID | Min 95 | 95-98 |

The basic common molecular structure of SBG and NBG, which represents preferred beta-glucans for use in the present invention, is as follows:

R=H or $(C_6H_{8-10}O_5)_{1-50}$; n=35-2000;

The preferred particulate beta-glucan of the present invention may be prepared in the following way:

By repeated extractions in alkali and acid of dry *Saccharomyces cerevisiae*, for example according to the procedure described in U.S. Pat. No. 5,401,727 (incorporated herein by reference). The extraction process described removes cytoplasmic components inside the yeast cells as well as the mannose containing polysaccharides and proteoglycans which are on the cell surface. The product prepared according to this procedure consists of a beta-1,3 beta-1,6-glucan with a particle size of 2-5 micrometers. The chemical structure of this micro-particulate beta-1,3 beta-1,6-glucan is characterized by 83% beta-1,3 linked glucose, 6% beta-1,6 linked and 5% beta-1,3,6 linked glucose, and it is a beta-1,3-glucan chain with beta-1,3,6-linked glucose as the branch points.

The particulate glucans of the present invention have a molecular weight in the range of 5000 Da to 1,000,000 Da, preferably in the range of 25 kDa to 500 kDa, more preferably in the range of 150 kDa to 300 kDa and most preferably about 250 kDa.

The particulate glucans described above may be solubilized as described in WO/2001/062283 (incorporated herein by reference). Thus, formic acid can be used to both reduce the number of beta-(1,6)-linked glucosyl residues in the glucan and to solubilize the glucan.

Other structures and/or structural conformations within the family of beta-1,3-glucans can be readily identified or isolated by a person of ordinary skill in the art following the teaching of this invention. The above is thus a guideline to achieve a highly potent product, but is not a limitation towards even more potent products. Isolated structural elements of the complex mixture may have improved effects over the presently exemplified formulations when administered.

The beta-glucans used in accordance with the present invention have utility as safe, effective, therapeutic and/or prophylactic agents, either alone or as adjuvants, to enhance the immune response in humans and animals by inducing a local inflammatory response by stimulating or priming the systemic immune system to release certain biochemical mediators (e.g., IL-1, IL-3, IL-6, IL-17, TNF-α, and GM-CSF). This specific effect is unique to these beta-glucans while many similar glucans claim not to stimulate or prime the immune system in that manner.

Without wanting to be bound by theory, it is believed that the beta-glucans used in accordance with the present invention modulate the immune system in humans and animals by down-regulating the Th2 immune response and by up-regulating the Th1 immune response.

Suitable carriers or auxiliaries for use in formulating glucan containing compositions for use in the present invention include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. The pH and exact concentration of the various components of the composition are adjusted according to routine skills.

The compositions for medical and veterinary use are preferably prepared and administered in dose units. The term "dose units" and its grammatical equivalents as used herein refer to physically discrete units suitable as unitary dosages for the human or non-human subject, each unit containing a predetermined effective amount of glucan calculated to produce the desired therapeutic effect in association with the required physiologically tolerable carrier, e.g., a diluent or a vehicle.

The composition may comprise the active ingredient alone, in a form suitable for administration to a subject, or the composition will typically comprise the glucan and one or more physiologically acceptable carriers, one or more additional active ingredients, or some combination of these.

The formulations described herein may be prepared by any method known or hereafter developed in the art of pharmacology, veterinary science, animal and human nutrition etc. In general, such preparatory methods include the step of bringing the active ingredient into association with a carrier or one or more other accessory ingredients, and then, if necessary or desirable, shaping or packaging the product into a desired single or multi-dose unit. Controlled or sustained-release formulations of a composition of the present invention may be made using conventional technology.

Dosage levels of the active compounds comprised in the composition for use in the present invention may vary. Functional dose ranges of the glucans can be readily determined by one of ordinary skill in the art. For example, when administered orally the functional dose range and effective amount for a human would be in the region of 10-500 mg/kg b.w. (body weight)/day, preferably 50-300 mg/kg b.w./day. When administered parenterally a suitable functional dose range would be 0.1-10 mg/kg b.w./day.

The compositions according to the invention may be presented in the form of an article or carrier such as a tablet, coated tablet, lozenges, troches, syrups or elixirs, liposomes, powder/talc or other solid, solution, emulsions, suspension, liquid, spray, gel, drops, aerosol, douche, ointment, foam, cream, gel, paste, microcapsules, controlled release formulation, sustained release formulation or any other article or carrier which may possible or useful in light of the intended or preferred mode of administration.

The route(s) of administration will be readily apparent to the skilled artisan and will depend upon any number of factors including the type and severity of the disease being treated, the type and age of the subject being treated, and the like. The most preferred route of administration is orally, optionally by gavage. Formulations suitable for oral administration of the glucan (preferably soluble glucan) include, but are not limited to, an aqueous or oily suspension, an aqueous or oily solution, or an emulsion. Such formulations can be administered by any means including, but not limited to, soft gelatin capsules. Liquid formulations of a pharmaceutical composition of the present invention which are suitable for oral administration may be prepared, packaged, and sold either in liquid form or in the form of a dry product intended for reconstitution with water or other suitable vehicle prior to use. With regard to the particulate product, it is possible to use other means of administration including but not limited to capsules, tablets, powders, granules, lozenges, drops, suppositories or any other means of administration suitable for a particulate product. Other types of administration which are preferred are nasal administration, inhalation or any other easy-to-use application in case of an asthmatic attack. Whatever route is selected, preferably a systemic effect is achieved and the dose and method of administration is selected or designed with this objective in mind.

Therapy may be repeated intermittently while the symptoms are present or even when they are not present. It might be relevant to administer the components two weeks prior to the expected challenge and/or for several weeks after the challenge. Continuous use is also possible, as for the treatment of chronic conditions.

The glucan may be provided alone or in combination with other medicaments to provide an operative combination. Thus in a further embodiment is provided a product containing (a) a glucan as described above, and (b) a second active agent for the treatment of asthma or related diseases of abnormal pulmonary function, as a combined preparation for simultaneous, separate or sequential use in the treatment of asthma or related diseases of abnormal pulmonary function.

Thus, it is possible to use a single glucan, a combination of two or more glucans or, if applicable, a combination of glucan(s) and another medical substance. With regard to a composition including two or more glucans it is possible to use different glucans from the same or different species or from the same species but produced by different methods.

A skilled artisan/physician will be able to select the medical substances which can be applied together with glucans for treatment of the relevant condition. Examples of suitable additional medical substances are, but are not limited to, relief medication like bronchodilators, short-acting, selective beta2-adrenoceptor agonists, such as salbutamol (albuterol USAN), levalbuterol, terbutaline and bitolterol, adrenergic agonists such as inhaled epinephrine and ephedrine tablets, anticholinergic medications, such as ipratropium bromide, chromoglycate therapy; prevention medication like inhaled corticosteroid, inhaled glucocorticoids including ciclesonide, beclomethasone, budesonide, flunisolide, fluticasone, mometasone, and triamcinolone. Leukotriene modifiers (montelukast, zafirlukast, pranlukast, and zileuton). Mast cell stabilizers (cromoglicate (cromolyn), and nedocromil), Antimuscarinics/anticholinergics (ipratropium, oxitropium, and tiotropium), Methylxanthines (theophylline and aminophylline), Antihistamines, Omalizumab, Methotrexate; as well as alternative and different medication used in complementary medicine.

In general, the beta-glucan can be administered to an animal as frequently as several times daily, or it may be administered less frequently, such as once a day. The treatment will for instance depend upon the type of asthma or related disease, the severity of the condition, and the condition of each patient. The glucan treatment may be closely interrelated with any other treatment regimen, and could be ahead of, concurrent with, or after the administration of any other medicament.

The glucan or compositions of two or more glucans as described in the present invention may be applied as prophylaxis for prevention of asthmatic conditions in advance of an asthmatic attack or as a treatment after the asthmatic incidence has occurred. Thus, 'treatment' as used herein includes prophylactic treatment, i.e. prevention, both of an individual episode or attack and of the onset of the disease in a subject deemed at risk. Prophylactic treatment will usually be in relation to an attack/episode. 'Treatment' includes a measurable and beneficial improvement in one or more, preferably more than one symptom of or risk factor for asthma or a related disease of abnormal pulmonary function. Preferably in one or more symptoms and more preferably a conclusion by the patient and/or treating physician that the asthma or related disease is improved, either in terms of the historical presentation of the disease or what was anticipated (e.g. in the case of a prophylactic treatment).

The term "asthma" refers to a chronic or recurring inflammatory condition of the respiratory system in which the airway develops increased responsiveness to various stimuli, characterized by bronchial hyper-responsiveness, inflammation, increased mucus production, and intermittent airway obstruction, often in response to one or more triggers. These acute episodes may be triggered by such things as exposure to an environmental stimulant (or allergen), cold air, exercise or exertion, or emotional stress. Occupational asthma is included. The symptoms of asthma can range from mild to life threatening. Treatment will typically include an improvement in one or more of the above symptoms, by in bronchial inflammation or mucus production as well as a tendency towards more normal respiratory behavior in general.

Most advantageously the invention provides for an improvement in bronchial asthma, specifically with regard to a reduction in pulmonary inflammation and/or a reduction in airway airflow resistance. The Examples provide protocols for measurement of these parameters.

'Related diseases of abnormal pulmonary function' include those diseases where patients exhibit continuous or sporadic impaired pulmonary function, generally associated with restricted airflow and/or bronchial inflammation. Such related diseases include lung disease, exemplified, but not limited to, allergic bronchopulmonary aspergillosis, (chronic) bronchitis with an allergic element and emphysema.

The present invention also provides a method of treating asthma or a related disease of abnormal pulmonary function in a subject which comprises administrating an effective amount of a glucan as described above. Typically the subject will be an animal, preferably a human, who has been diagnosed with or being at risk of asthma (or said related disease).

This invention also provides a kit or an administration device comprising a glucan as described herein and information material which describes administering the glucan to a human or other animal. The kit or administration device may have a compartment containing the glucan. As used herein, the "Information material" includes, but is not limited to, a publication, a recording, a diagram, or any other medium of expression which can be used to communicate the usefulness of the composition of the invention for its designated use. Examples of administration devices are, but are not limited to, all types of inhalers, nebulisers and dry-powder devices.

Thus, in a further preferred embodiment, the invention provides an inhaler, nebuliser or dry-powder device containing a glucan as described herein in a form suitable for self-administration by a patient to treat or prevent an asthma attack. Such a device is typically designed for use by mouth. Thus, preferred devices have the glucan in solubilized liquid or dry powder form. Liquids may be under pressure and the device may have components which allow air or oxygen to pass through a predetermined amount of the glucan making it available for inhalation by the patient.

By "an effective amount" is meant an amount of a compound effective to ameliorate the symptoms of, or ameliorate, treat, prevent, delay the onset of or inhibit the progression of a disease. Ultimately, the attending physician or veterinarian will decide the appropriate amount and dosage regimen. The "effective amount" of the active ingredients that may be combined with the carrier materials to produce a single dosage will vary depending upon the subject treated and the particular mode of administration.

Various documents including, for example, publications and patents, are recited throughout this disclosure. All such documents are, in relevant part, hereby incorporated by reference. The citation of any given document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

Referenced herein are trade names for components including various ingredients utilized in the present invention. The inventors herein do not intend to be limited by materials under a certain trade name. Equivalent materials (e.g., those obtained from a different source under a different name or reference number) to those referenced by trade name may be substituted and utilized in the descriptions herein.

The compositions described herein may comprise, consist essentially of, or consist of any of the elements as described herein.

In a further aspect the present invention provides for the use of the glucans and formulations described above in the manufacture of a medicament for treating autoimmune diseases which are characterized by the body's immune responses being directed against its own tissues, causing prolonged inflammation and subsequent tissue destruction. Such diseases comprise all diseases where a shift of Th1/Th2 reaction patterns towards a more pronounced Th2-pattern is an essential element of the pathogenesis. Examples for these autoimmune diseases are, but are not limited to, celiac disease, Crohn's disease, pancreatitis, systemic lupus erythematosus, Sjogren's syndrome, Hashimoto's thyroiditis, and other endocrinopathies. Multiple sclerosis is also a part of this group. Equivalent methods of medical treatment are also provided.

In a preferred further aspect the present invention provides for the use of the glucans and formulations described above in the manufacture of a medicament for treating allergic rhinitis (hay fever). Equivalent methods of medical treatment are also provided. The efficacy of the glucans in this therapeutic context is demonstrated in the Examples hereto.

In a further aspect the present invention provides for the use of the glucans and formulations described above in the manufacture of a medicament for treating allergies. Allergies include mold spores, drugs, foods (in particular nuts, sesame, seafood, egg, soy, milk, wheat and maize), insect stings, laytex and animal products (especially animal hair and dander, cockroach calyx and dust mite excretion. Equivalent methods of medical treatment are also provided.

The following examples are intended to be illustrative of the present invention and to teach one of ordinary skill in the art to make and use the invention. These examples are not intended to limit the invention in any way. The invention will now be further described in the following Examples and the figures in which.

TABLE 1

| Chemical shift (ppm) | Assignment | Comment |
|---|---|---|
| 5.00 | H1 RT(α) | H1 in the α-anomer for the reducing terminus (RT) |
| 4.54 | H1 BC | H1 in backbone chain of (1-3)-linked glucosyl repeat units (GRUs) |
| 4.39 | H1 NRT + H1 RT(β) | H1 in the non-reducing terminus (NRT) + in the β-anomer of the reducing terminus (RT) |
| 4.27 | H1 (1-6) SC | H1 in (1-6)-linked side-chains |
| 4.03 | H6 (1-6) SC | H6 in (1-6)-linked side-chains |
| 3.72 | H6 BC | H6 in the backbone chain of (1-3)-linked glucosyl repeat units (GRUs) |
| 3.48 | H3 BC + H6' BC | H3 and H6' in the backbone chain of (1-3)-linked glucosyl repeat units (GRUs) |
| 3.30-3.24 | H2 BC + H4 BC + H5 BC | H2, H4 and H5 in the backbone chain of (1-3)-linked glucosyl repeat units (GRUs) |
| 3.09 | H2 NRT | H2 in the non-reducing terminus (NRT) |
| 3.02 | H2 (1-6) SC | H2 in (1-6) linked side-chains |
| 2.54 | DMSO | The solvent peak |

EXAMPLES

Example 1

Five-week-old AKR mice were pre-treated with oral β-glucan daily for 5 consecutive days weekly, for 4 weeks prior to sensitization—particulate 1 mg, particulate 6 mg, water-soluble 1 mg, or water-soluble 6 mg. They continued treatment throughout the sensitization and challenge phase. Sham treated mice received an equivalent volume of water. Naïve mice served as negative controls. β-glucan treated mice and sham treated mice were then intraperitoneally sensitized to ovalbumin (OVA) and aluminium hydroxide twice at a 7 day interval, followed by 4 sets of intratracheal challenges at 7-10 day intervals with OVA. Bronchoalveolar lavage fluid (BALF) were then taken and differential counts made.

TABLE 2

| | Absolute Leukocyte Count in BALF | Mean Percent Eosinophils in BALF |
|---|---|---|
| Sham | $15.4 \times 10^4 \pm 1.72 \times 10^4$ | $20.33\% \pm 7.1\%$ |
| Particulate 1 mg | $5 \times 10^4 \pm 1.18 \times 10^4$ | $3.2\% \pm 2.9\%$, |
| Particulate 6 mg | $11.14 \times 10^4 \pm 1.8 \times 10^4$ | $1.3\% \pm 0.5\%$ |
| Soluble 1 mg | $3.8 \times 10^4 \pm 0.37 \times 10^4$ | $2.1\% \pm 1.5\%$ |
| Soluble 6 mg | $4 \times 10^4 + 1.5 \times 10^4$ | $6.2\% \pm 4.2\%$ |
| Naïve | $2.2 \times 10^4 \pm 0.2 \times 10^4$ | $0.1\% \pm 0.01\%$ |

Absolute leukocyte counts in BALF were increased in sham treated mice ($15.4 \times 10^4 \pm 1.72 \times 10^4$ P<0.001) compared to naïve mice ($2.2 \times 10^4 \pm 0.2 \times 10^4$ P<0.001). Absolute leukocyte counts in BALF were decreased in all treated groups compared to sham (particulate 1 mg $5 \times 10^4 \pm 1.18 \times 10^4$, P<0.001; particulate 6 mg $11.4 \times 10^4 \pm 1.8 \times 10^4$, P<0.001; soluble 1 mg $3.8 \times 10^4 \pm 0.37 \times 10^4$, P<0.001; soluble 6 mg $4 \times 10^4 \pm 1.5 \times 10^4$<P0.001). The mean percent eosinophils in BALF of sham treated mice ($20.33\% \pm 7.1\%$, P<0.008) were elevated compared to naïve ($0.1\% \pm 0.01\%$, P<0.008). The mean percent eosinophils in BALF of treated mice were decreased compared to sham treated mice (particulate 1 mg $3.2\% \pm 2.9\%$, P=0.011; particulate 6 mg $1.3\% \pm 0.5\%$ P=0.006; soluble 6 mg $6.2\% \pm 4.2\%$, P=0.17).

Example 2

Five week-old AKR mice were pre-treated with oral β-glucan daily for 5 consecutive days weekly, for 4 weeks prior to sensitization, particulate 1 mg, particulate 6 mg, water-soluble 1 mg, or water-soluble 6 mg. They continued treatment throughout the sensitization and challenge phase. Sham treated mice received an equivalent volume of water. Naïve mice served as negative controls. β-glucan treated mice and sham treated mice were then intraperitoneally sensitized to ovalbumin (OVA) and aluminium hydroxide twice at a 7 day interval, followed by 4 sets of intratracheal challenges at 7-10 day intervals with OVA. Airway pressure time index (APTI) was recorded. 72 hours following the last i.t. challenge, airway responsiveness was determined by measuring airway pressure changes following intravenous (i.v.) acetylcholine (Ach) challenge. Briefly, mice were anaesthetized with sodium pentobarbital (80 mg/kg), and ventilated via a tracheal cannula (18 gauge) at the rate of 120 per minute with a consistent tidal volume of air (0.2 ml) with RSP 1002 Pressure Controlled Respirator System (IKent Scientific Corporation, CT). Muscle paralysis was provided by i.v. administration of decamethonium bromide (25 mg/kg). Airway pressure was measured with a pressure transducer via a port in the trachea. Two minutes after establishing a stable airway pressure recording. Ach was injected i.v. (50 μg/kg). Airway pressure changes were then viewed and recorded, and pulmonary parameters were generated with the software respiratory data acquisition system VENTP (Kent Scientific Corporation, CT). The time-integrated changes in peak airway pressure referred to as the airway pressure-time index (APTI; cm $H_2O$ per second) was calculated and served as the measurements of airway responsiveness.

TABLE 3

| | APTI |
|---|---|
| Sham | $517.98 \pm 27.65$ |
| Particulate 1 mg | $267.86 \pm 27.80$ |
| Particulate 6 mg | $284.36 \pm 18.76$ |
| Soluble 1 mg | $210.46 \pm 13.92$ |
| Soluble 6 mg | $524.25 \pm 98.35$ |
| Naïve | $145.74 \pm 24.76$ |

APTI was increased in sham-treated mice ($517.98 \pm 27.55$, P<0.001) compared to naïve mice ($145.74 \pm 24.76$, P<0.001). All β-glucan-treated mice (particulate 1 mg $267.86 \pm 27.80$, P<0.001; particulate 6 mg $284.36 \pm 18.76$, P<0.001; soluble 1 mg $210.46 \pm 13.92$ P<0.001) had decreased APTI compared with sham treated mice, with exception to water-soluble β-glucan 6 mg treated mice $524.25 \pm 98.35$ P1).

Example 3

Five week-old AKR mice were pre-treated with oral β-glucan daily for 5 consecutive days weekly, for 4 weeks prior to sensitization, particulate 1 mg, particulate 6 mg, water-soluble 1 mg, or water-soluble 6 mg. They continued treatment throughout the sensitization and challenge phase. Sham treated mice received an equivalent volume of water. Naïve mice served as negative controls. β-glucan treated mice and sham treated mice were then intraperitoneally sensitized to ovalbumin (OVA) and aluminium hydroxide twice at a 7 day interval, followed by 4 sets of intratracheal challenges at 7-10 day intervals with OVA.

Murine splenocytes were cultured with ovalbumin (OVA) and the supernatants were assessed for cytokine levels by Elisa. Splenocytes from mice treated with 1 mg water soluble SBG had decreased production of IL5 compared with sham treated mice without SBG (199,67 pg/ml versus 297.86 pg/ml, p<0.01) Splenocytes from mice treated with 1 mg granular NBG had decreased IL5 production as compared with sham treated mice stimulated with OVA (134.85 pg/ml versus 297.86 pg/ml, p<0.01). Similarly, splenocytes from mice treated with both two beta-glucan preparations showed reduced production of IL-13 as compared to splenocytes from sham treated mice.

Example 4

Five week-old AKR mice were pre-treated with oral β-glucan daily for 5 consecutive days weekly, for 4 weeks prior to sensitization, particulate 1 mg, particulate 6 mg, water-soluble 1 mg, or water-soluble 6 mg. They continued treatment throughout the sensitization and challenge phase. Sham treated mice received an equivalent volume of water. Naïve mice served as negative controls. β-glucan treated mice and sham treated mice were then intraperitoneally sensitized to ovalbumin (OVA) and aluminium hydroxide twice at a 7 day interval, followed by 4 sets of intratracheal challenges at 7-10 day intervals with OVA.

Murine splenocytes were cultured with ovalbumin (OVA) and the culture supernatants were collected after 72 hour culture and assessed for cytokine levels by Elisa. The cytokine levels to OVA stimulation were normalized by subtracting the respective cytokine levels from medium alone.

Figure 11:
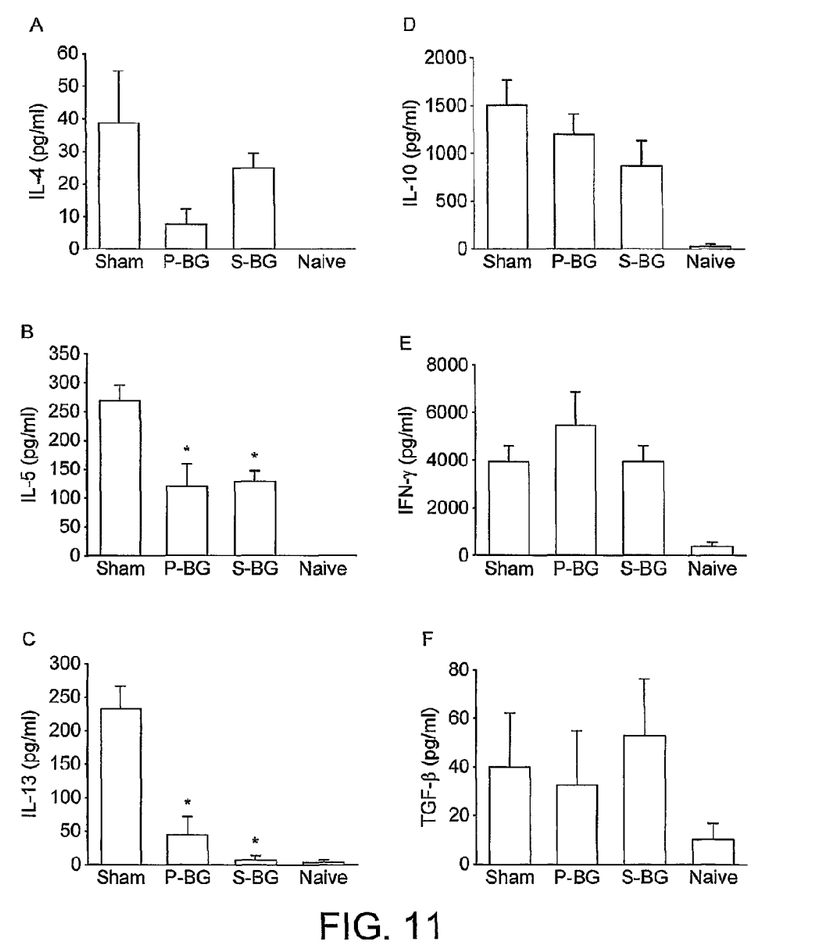
FIG. 11 is a graph showing the effect of glucan (SBG and NBG) treatment of five week-old AKR mice on the production of various cytokines as compared to sham treated and naïve mice as determined by ELISA.

As compared to the sham-treated group, P-BG and S-BG reduced IL-4 by 82% and 36% respectively reduced IL-5 by 56% and 54% respectively and reduced IL-13 by 81% and 96% respectively (FIG. 11). There were no significant differences in IL-10, IFN-γ and TGF-β levels between the P-BG or S-BG treated groups and sham-treated groups (FIG. 11).

Example 5

Five week-old AKR mice were pre-treated with oral β-glucan daily for 5 consecutive days weekly, for 4 weeks prior to sensitization, particulate 1 mg, particulate 6 mg, water-soluble 1 mg, or water-soluble 6 mg. They continued treatment throughout the sensitization and challenge phase. Sham treated mice received an equivalent volume of water. Naïve mice served as negative controls. β-glucan treated mice and sham treated mice were then intraperitoneally sensitized to ovalbumin (OVA) and aluminium hydroxide twice at a 7 day interval, followed by 4 sets of intratracheal challenges at 7-10 day intervals with OVA.

Figure 12:
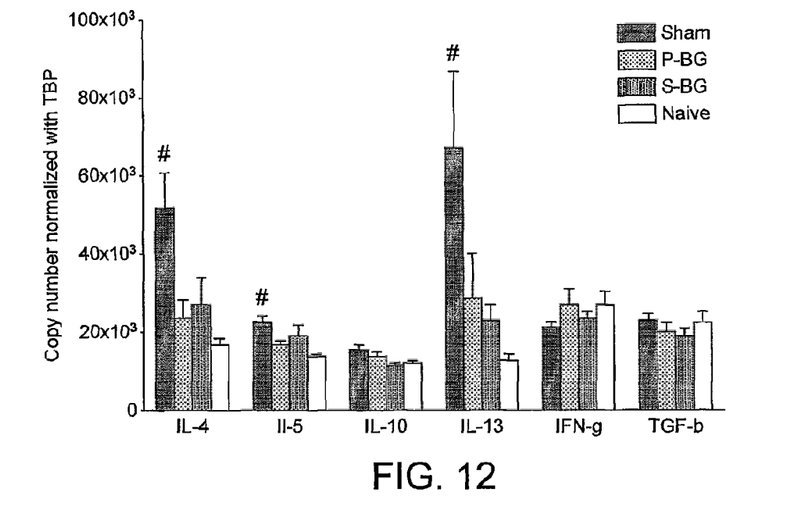
FIG. 12 is a graph showing the effect of glucan (SBG and NBG) treatment of five week-old AKR mice on the lung mRNA levels of various cytokines as compared to sham treated and naïve mice as determined by quantitative real-time PCR.

The effect of BG on cytokine profiles of lungs from different groups of mice were determined by evaluating cytokine mRNA levels using quantitative real-time PCR (FIG. 12). IL-4, IL-5 and IL-13 mRNA levels were increased 3, 1 and 7 fold respectively in the sham treated group compared to the naïve group indicating a Th2 mediated response. In contrast, in both of the BG-treated groups, the Th2 mRNA levels, in particular Il-4 and IL-13 levels, were reduced compared with the sham treated group. Il-4 was reduced by 55% and 48% in the P-BG and S-BG groups respectively. IL-13 was reduced by 40% and 53% in the P-BG and S-BG groups respectively. However, there were no differences in IL-10, IFN-7 and TGF-β transcript levels between the treated groups and the sham treated group.

Example 6

Five week-old AKR mice were pre-treated with oral β-glucan daily for 5 consecutive days weekly, for 4 weeks prior to sensitization, particulate 1 mg, particulate 6 mg, water-soluble 1 mg, or water-soluble 6 mg. They continued treatment throughout the sensitization and challenge phase. Sham treated mice received an equivalent volume of water. Naïve mice served as negative controls. β-glucan treated mice and sham treated mice were then intraperitoneally sensitized to ovalbumin (OVA) and aluminium hydroxide twice at a 7 day interval, followed by 4 sets of intratracheal challenges at 7-10 day intervals with OVA.

Figure 13:
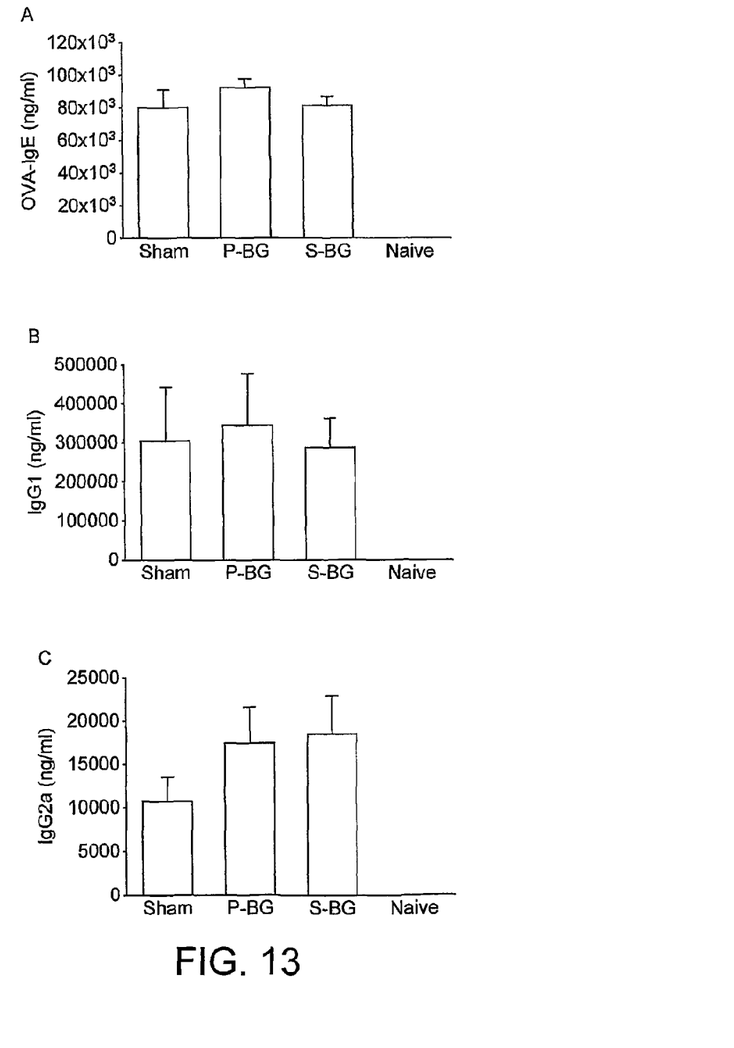
FIG. 13 is a graph showing the effect of glucan (SBG and NBG) treatment of five week-old AKR mice on OVA-specific serum IgE, IgG1 and IgG2a levels as compared to sham treated and naïve mice as determined by ELISA.

Approximately 100 μl of blood was obtained via retro-orbital puncture immediately prior to APTI. Plasma antigen-specific IgE, IgG1 and IgG2a levels were determined by ELISA. There was no statistically significant difference in OVA-specific IgE, IgG1 or IgG2a levels between the BG treated and sham treated groups (FIG. 13).

The above examples demonstrate that both NBG treatment and SBG treatment significantly reduce the allergic pulmonary inflammation typical of bronchial asthma, and reduces significantly the airway airflow resistance typical of bronchial asthma.

Increased airway resistance (hyperactivity) is the defining element of bronchial asthma and related diseases. Our results demonstrate that oral administration of water soluble or granular (particulate) β1-3 glucan reduces hyperactivity and thus appears to be an effective treatment/prophylaxis for asthmatic conditions, probably by shifting an immune reaction in the lung from a Th$_2$ type in the direction of a Th$_1$, type. The exact mechanism is not established. It is known, however, that β1-3 glucan stimulates cells of the mononuclear phagocyte lineage to produce a series of cytokines that may influence lymphocyte production of Il-4 and IFN-γ, pivotal for the Th$_1$/Th$_2$ balance.

The granular/particulate β1-3 glucan was effective at both dosages tested and suggests an expected dose-effect relationship. The soluble β1-3 glucan, however, had a stronger effect at the lower dose—which may suggest a narrower effective dose range, or stimulation of inhibitory substances at higher concentrations.

The Examples show that S-BG and P-BG treatment suppressed Th2 responses with no significant effect on Th1 or T regulatory (IL-10) or cytokine-3 (TGF-β). This finding suggests that the prophylactic effect of both S-BG and P-BG on AHR and pulmonary inflammation is associated with down-regulation of Th2 responses. However, BG had no statistically significant effect on the OVA-specific immunoglobulins, IgE, IgG1 or IgG2a which indicates that the majority of the effect of β-glucan is on T-cells.

Example 7

Figure 2:
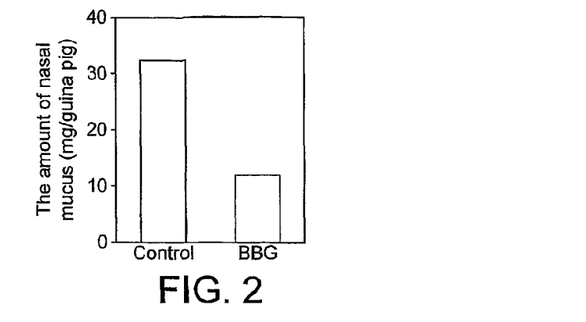
FIG. 2 is a graph showing the influence of glucan (BBG) on nasal mucosa.
Figure 3:
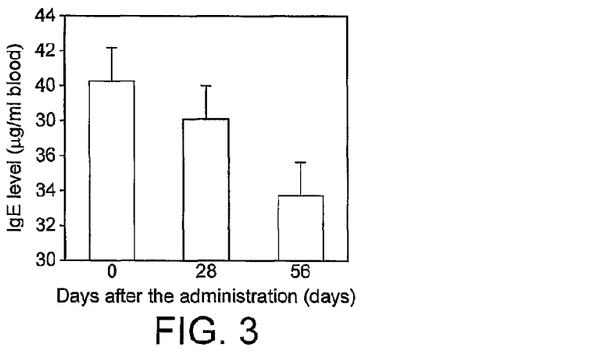
FIG. 3 is a graph showing the influence of glucan (BBG) on IgE levels in blood over time.
Figure 4:
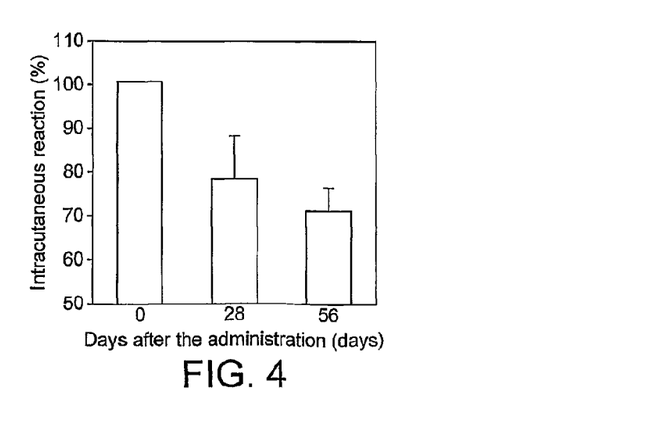
FIG. 4 is a graph showing the effect of glucan (BBG) on intracutaneous reaction over time.
Figure 5:
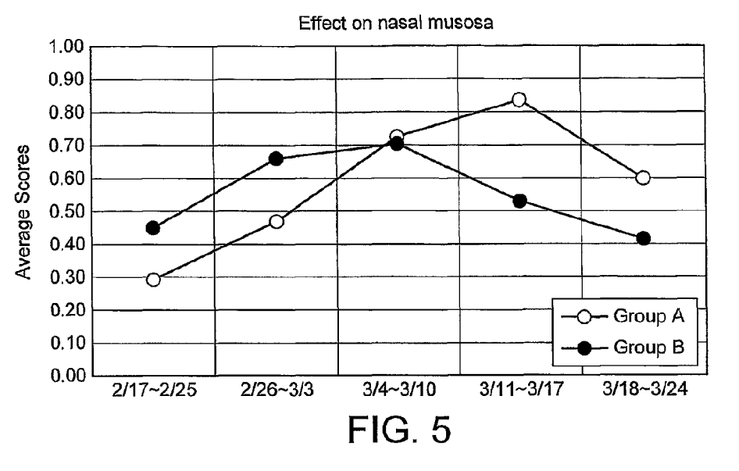
FIG. 5 is a graph showing the effect of glucan (NBG) administration on the condition of the nasal mucosa.
Figure 6:
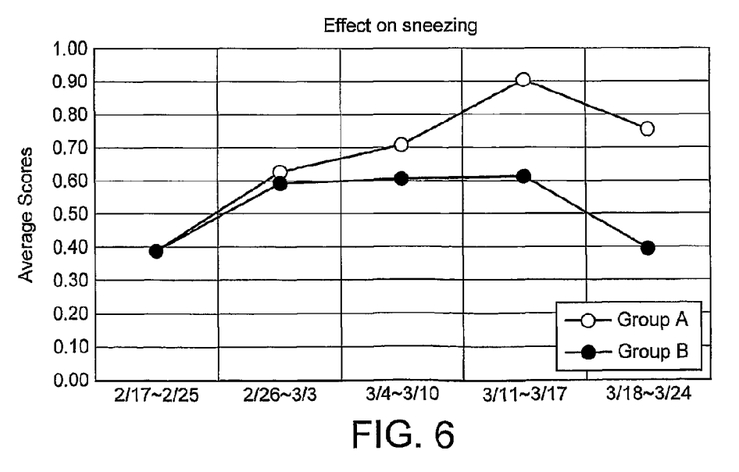
FIG. 6 is a graph showing the effect of glucan (NBG) administration on the frequency of sneezing.
Figure 7:
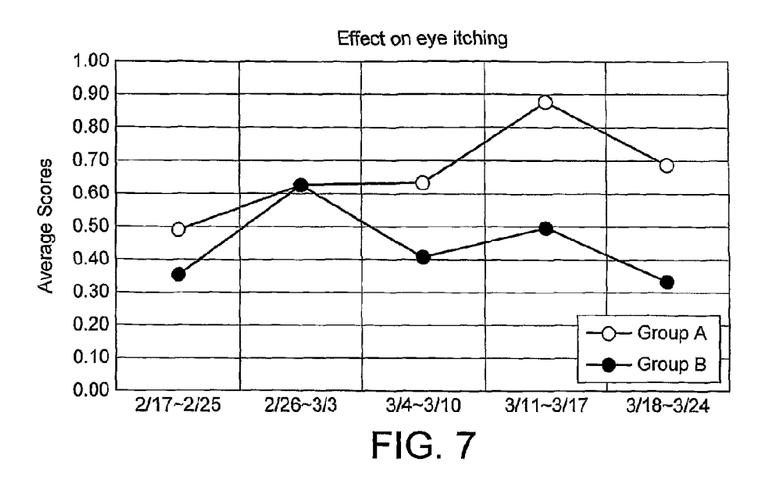
FIG. 7 is a graph showing the effect of glucan (NBG) administration on eye itching.
Figure 8:
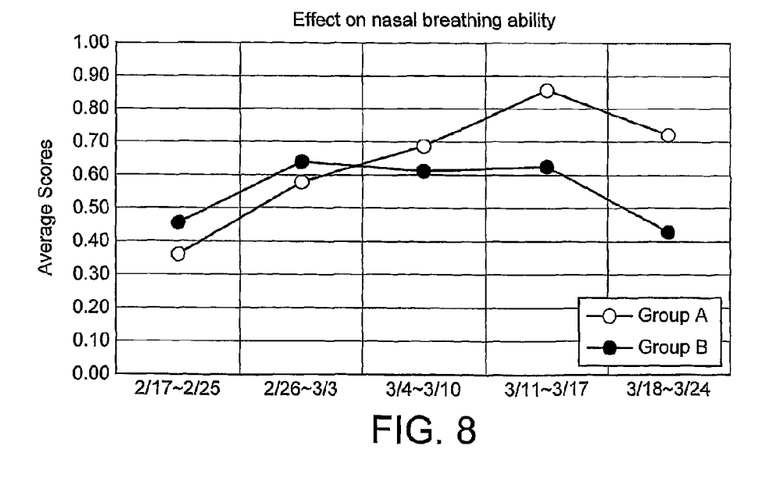
FIG. 8 is a graph showing the effect of glucan (NBG) administration on the nasal breathing ability.
Figure 9:
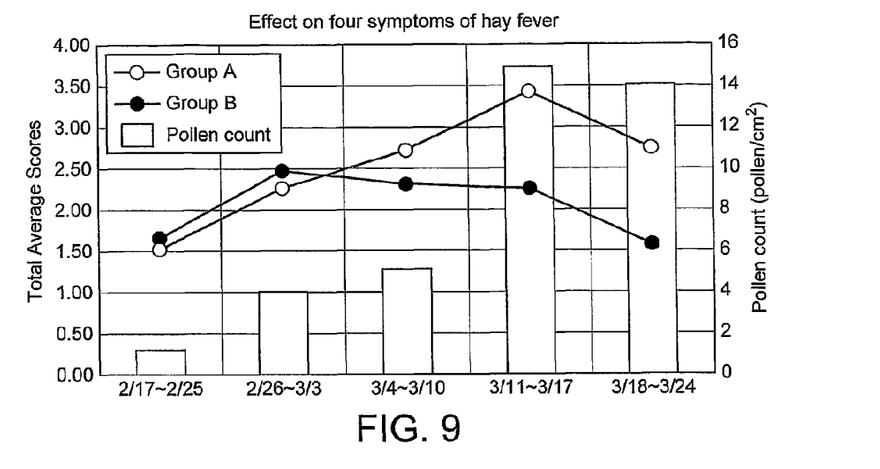
FIG. 9 is a graph showing the total effect of (NBG) glucan administration on all four symptoms of hay fever combined. In addition the pollen presence in that specific time period was obtained and included in the figure.
Figure 10:
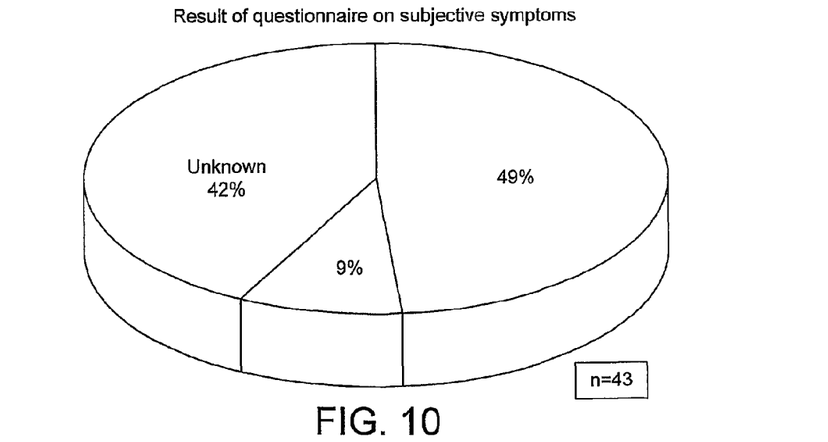
FIG. 10 is a chart showing the results of a questionnaire on all 9 subjective symptoms. (9% no effect, 49% effect, 42% uncertain.

BBG (the same glucan product as NBG defined herein) was tested in the following scenarios
A: Inhibitory Effect of BBG on Nasal Mucus Secretion
Method:
Toluene-2,4-diisocynate (TDI)-sensitized guinea pigs were used as an allergic rhinitis model. The amount of nasal mucus was measured after oral administration of BBG.
Result & Conclusion:
The amount of nasal mucus of BBG-ingested group was 66.7% lower than that of the control group (FIG. 2).
B: Improvement of Symptoms of Cedar Pollen-Induced Allergic Rhinitis
Method:
BBG had been administered to cedar pollen-sensitized beagles during 57 days. IgE levels in blood and intracutaneous reaction were examined.
Result & Conclusions:
IgE levels in blood were reduced during administration (FIG. 3). Approximately 30% reduction of average scores was admitted after 56 days (FIG. 4), approximately 60% reduction after 168 days. The results indicate improvement of allergic reaction with BBG.

Example 8

A study on the effect of the glucan (NBG) towards hay fever was conducted. In the study, 43 probants were given 500 mg of the particulate glucan product. The probants took 125 mg of the product 4 times a day (in total 500 mg/day) p.o. Half the study population was given the product for the first 18 days (Group A), whereas the remaining took the product for 37 days (Group B). Based on self-evaluation (a subjective measurement resulting in "scores") of a number of 4 parameters being an evaluation of the condition of the nasal mucosa, the frequency of sneezing, the effect on eye itching and nasal breathing ability; as well as 5 more general parameters like i.e. physical condition, appetite, sleep, there was a marked difference between the two groups. Overall, about half of the total study population (i.e. both groups combined) claimed effect. The scores obtained in that study were a summary of all parameters, meaning a score of 1.00 indicates that the probant is still afflicted by the symptoms, while a score of 0.00 shows that the probants have no further symptoms after taking the glucan product.

The results of these studies are presented in FIGS. 5-10.

The invention claimed is:

1. A method of inhibiting a symptom of hay fever in a human subject in need thereof comprising the oral administration to said human subject a glucan having a beta-(1,3)-backbone with one or more beta-(1,3)-side chains linked thereto in an effective dose range of 10 to 500 mg per kg body weight per day, wherein the glucan is isolated from other cell wall components and wherein said symptom is selected from the group consisting of eye itching, nasal breathing difficulty, nasal mucus secretion and sneezing.

2. The method according to claim 1, wherein the source of glucan is selected from the group consisting of yeast, mushrooms or other fungi, Gramineae, algae and bacteria.

3. The method according to claim 2 wherein the yeast is *Saccharomyces cerevisiae*.

4. The method according to claim 1, wherein the glucan is underivatized by chemical groups.

5. The method according to claim 1, wherein the glucan contains less than 2% of repetitive beta-(1,6)-linked glucosyl units.

6. The method according to claim 1, wherein the glucan is in particulate form.

7. The method according to claim 1, wherein the glucan is solubilized.

8. The method according to claim 6 wherein the molecular weight of the glucan is in the range of 150 kDa to 300 kDa.

9. The method according to claim 7 wherein the molecular weight of the glucan is in the range of about 6 kDa to 30 kDa.

* * * * *